US008324192B2

(12) United States Patent
Dohil et al.

(10) Patent No.: US 8,324,192 B2
(45) Date of Patent: Dec. 4, 2012

(54) VISCOUS BUDESONIDE FOR THE TREATMENT OF INFLAMMATORY DISEASES OF THE GASTROINTESTINAL TRACT (75) Inventors: Ranjan Dohil, San Diego, CA (US); John Bastian, San Diego, CA (US); Seema S. Aceves, Solana Beach, CA (US)

(73) Assignee: The Regents of the University of California, Oakland, CA (US)

( * ) Notice: Subject to any disclaimer, the term of this patent is extended or adjusted under 35 U.S.C. 154(b) by 870 days.

(21) Appl. No.: 11/595,513

(22) Filed: Nov. 9, 2006

(65) Prior Publication Data
US 2007/0111978 A1 May 17, 2007

Related U.S. Application Data (60) Provisional application No. 60/735,340, filed on Nov. 12, 2005.

(51) Int. Cl.
*A61K 31/56* (2006.01)
(52) U.S. Cl. .................. 514/170; 514/180; 514/182
(58) Field of Classification Search .................. 514/170, 514/180, 182
See application file for complete search history.

(56) References Cited

U.S. PATENT DOCUMENTS

| 2,861,920 | A | 11/1958 | Dale et al. |
| 4,684,534 | A | 8/1987 | Valentine |
| 4,900,552 | A | 2/1990 | Sanvordeker et al. |
| 5,288,497 | A | 2/1994 | Stanley et al. |
| 5,446,070 | A | 8/1995 | Mantelle |
| 5,585,108 | A | 12/1996 | Ruddy |
| 5,643,602 | A | 7/1997 | Ulmius |
| 5,711,936 | A | 1/1998 | Hill et al. |
| 5,763,910 | A | 6/1998 | Ema |
| 5,814,330 | A | 9/1998 | Putteman et al. |
| 5,837,713 | A | * 11/1998 | Gleich ........................ 514/312 |
| 5,863,910 | A | 1/1999 | Bolonick et al. |
| 5,889,028 | A | 3/1999 | Sandborn et al. |
| 6,028,095 | A | 2/2000 | Guglietta |
| 6,291,445 | B1 | 9/2001 | Nilsson et al. |
| 6,306,789 | B1 | 10/2001 | Dettmar et al. |
| 6,348,502 | B1 | 2/2002 | Gardiner et al. |
| 6,387,383 | B1 | 5/2002 | Dow et al. |
| 6,509,028 | B2 | 1/2003 | Williams et al. |
| 6,562,363 | B1 | 5/2003 | Mantelle et al. |
| 6,589,551 | B1 | 7/2003 | Jolliffe |
| 6,589,556 | B2 | 7/2003 | Cherukuri |
| 6,596,261 | B1 | 7/2003 | Adjei et al. |
| 6,638,521 | B2 | 10/2003 | Dobrozsi |
| 6,787,529 | B2 | 9/2004 | Hoy et al. |
| 6,899,099 | B2 | 5/2005 | Andersson et al. |
| 6,916,485 | B2 | 7/2005 | Aiache et al. |
| 6,923,988 | B2 | 8/2005 | Patel et al. |
| 6,986,904 | B2 | 1/2006 | Nilsson et al. |
| 7,063,862 | B2 | 6/2006 | Lin et al. |
| 7,229,641 | B2 | 6/2007 | Cherukuri |
| 7,288,267 | B2 | 10/2007 | Bosch et al. |
| 7,361,646 | B2 | 4/2008 | Belanoff |
| 7,544,348 | B2 | 6/2009 | Jacob et al. |
| 7,547,433 | B2 | 6/2009 | Jacob et al. |
| 2001/0029255 | A1 | 10/2001 | Lindberg et al. |
| 2001/0049366 | A1 | 12/2001 | Singh et al. |
| 2002/0132803 | A1 | 9/2002 | Dedhiya et al. |
| 2002/0168334 | A1 | 11/2002 | Jacob et al. |
| 2003/0013693 | A1 | 1/2003 | Guivarc'h et al. |
| 2003/0017189 | A1 | 1/2003 | Wong et al. |
| 2003/0055028 | A1 | 3/2003 | Stergiopoulos et al. |
| 2003/0073676 | A1 | 4/2003 | Biggadike et al. |
| 2003/0192533 | A1 | 10/2003 | Andersson et al. |
| 2003/0215496 | A1 | 11/2003 | Patel et al. |
| 2004/0023935 | A1 | 2/2004 | Banerjee et al. |
| 2004/0028919 | A1 | 2/2004 | Yamamoto et al. |
| 2004/0053894 | A1 | 3/2004 | Mazess et al. |
| 2004/0141949 | A1 | 7/2004 | Rosenthal et al. |
| 2005/0042282 | A1 | 2/2005 | Leni |
| 2005/0049459 | A1 | 3/2005 | Hern |
| 2005/0079138 | A1 | 4/2005 | Chickering et al. |
| 2005/0152847 | A1 | 7/2005 | Trofast et al. |
| 2005/0153946 | A1 | 7/2005 | Hirsh et al. |
| 2005/0208110 | A1 | 9/2005 | Singh et al. |
| 2005/0239845 | A1 | 10/2005 | Proehl et al. |
| 2005/0281772 | A1 | 12/2005 | Bromley et al. |
| 2005/0287181 | A1 | 12/2005 | Murthy |
| 2006/0013873 | A1 | 1/2006 | Yang et al. |
| 2006/0024238 | A1 | 2/2006 | Barth |
| 2006/0128655 | A1 | 6/2006 | Falk et al. |
| 2006/0193783 | A1 | 8/2006 | Bhowmick et al. |

(Continued)

FOREIGN PATENT DOCUMENTS

EP 1201242 A2 5/2002

(Continued)

OTHER PUBLICATIONS

DeMuth, J. Allergy Clin. Immunlo., Feb. 2004.; 113(2 Suppl);S316.*
Pulmicort tubuhaler monograph, AstraZeneca, Dec. 2001.*
Furuta, Journal of Pediatric Gastroenterology & Nutrition, 1998;26(4):468-471.*
Garcia et al., Dysphagia 20:325-335 (2005).*
Noureddini et al. JAOCS, 69(12):1189-1191 (1992).*
Batchelor et al., "An in vitro mucosal model for prediction of the bioadhesion of alginate solutions to the oesophagus", International Journal of Pharmaceutics, vol. 238 (2002) pp. 123-132.
Batchelor et al., "Feasiblity of a bioadhesive drug delivery system targeted to oesophageal tissue", European Journal of Pharmaceutics and Biopharmaceutics, vol. 57 (2004) pp. 295-298.
Batchelor, "Bioadhesive dosage forms for esophageal drug delivery", Pharmaceutical Research, vol. 22, No. 2, Feb. 2005 (2004) pp. 175-181.
Christrup et al., "Deposition of a model substance, 99mTc E-HIDA, in the oral cavity after administration of lozenges, chewing gum and sublingual tablets", International Journal of Pharmaceutics, vol. 66, (1990) pp. 169-174.

(Continued)

Primary Examiner — San-Ming Hui
(74) Attorney, Agent, or Firm — Kilpatrick Townsend & Stockton LLP (57) ABSTRACT Provided herein are methods for preventing or alleviating the symptoms of and inflammation associated with inflammatory diseases and conditions of the gastrointestinal tract, for example, those involving the esophagus. Also provided herein are pharmaceutical compositions useful for the methods of the present invention.

50 Claims, 3 Drawing Sheets

U.S. PATENT DOCUMENTS

| | | |
|---|---|---|
| 2006/0216353 A1 | 9/2006 | Liversidge et al. |
| 2006/0235053 A1 | 10/2006 | Gebauer |
| 2007/0031459 A1 | 2/2007 | Asotra |
| 2007/0111978 A1 | 5/2007 | Dohil et al. |
| 2007/0134280 A1 | 6/2007 | Roman et al. |
| 2007/0248548 A1 | 10/2007 | Blondino et al. |
| 2007/0259037 A1 | 11/2007 | Guiverc'h et al. |
| 2008/0008762 A1 | 1/2008 | Robinson et al. |
| 2008/0132580 A1 | 6/2008 | Mandavilli et al. |
| 2008/0207771 A1 | 8/2008 | Dikstein |
| 2009/0123390 A1 | 5/2009 | Hill et al. |
| 2009/0123550 A1 | 5/2009 | Phillips et al. |
| 2009/0123551 A1 | 5/2009 | Phillips et al. |
| 2009/0131386 A1 | 5/2009 | Phillips et al. |
| 2009/0137540 A1 | 5/2009 | Phillips et al. |
| 2009/0143343 A1 | 6/2009 | Hill et al. |
| 2009/0149433 A1 | 6/2009 | Phillips et al. |
| 2009/0181099 A1 | 7/2009 | Dohil et al. |
| 2009/0264392 A1 | 10/2009 | Warndahl |

FOREIGN PATENT DOCUMENTS

| | | |
|---|---|---|
| EP | 1428526 A1 | 12/2002 |
| EP | 1795183 A1 | 8/2006 |
| WO | WO99/18938 A1 | 4/1999 |
| WO | WO99/32156 A2 | 7/1999 |
| WO | WO99/39699 | 8/1999 |
| WO | WO99/40906 | 8/1999 |
| WO | WO00/010528 | 3/2000 |
| WO | WO01/37808 | 5/2001 |
| WO | WO01/41748 | 6/2001 |
| WO | WO02/24205 | 3/2002 |
| WO | WO02/34235 | 5/2002 |
| WO | WO02/064113 | 8/2002 |
| WO | WO02/074316 | 9/2002 |
| WO | WO03/057194 | 7/2003 |
| WO | WO2004/030652 | 4/2004 |
| WO | WO2004/045612 A1 | 6/2004 |
| WO | WO2004/069225 | 8/2004 |
| WO | WO2004/082590 | 9/2004 |
| WO | WO2005/056066 | 6/2005 |
| WO | WO2005/065185 | 7/2005 |
| WO | WO2005/074930 | 8/2005 |
| WO | WO2005/120517 | 12/2005 |
| WO | WO2006/009825 | 1/2006 |
| WO | WO2006/035418 A2 | 4/2006 |
| WO | WO2006/048736 A1 | 5/2006 |
| WO | WO2006/085101 A2 | 8/2006 |
| WO | WO2006/099591 A1 | 9/2006 |
| WO | WO2007/061803 | 5/2007 |
| WO | WO2007/075475 | 7/2007 |
| WO | WO2007/096906 | 8/2007 |
| WO | WO2008/070129 A2 | 6/2008 |
| WO | WO2008/091855 | 7/2008 |

OTHER PUBLICATIONS

Dobrozsi et al., "Comparative mucoretention of sucralfate suspensions in an everted rat esophagus model", Internation Journal of Pharmaceutics, vol. 189 (1999) pp. 81-89.

Hardy et al., "A comparison of the gastric retention of a sucralfate gel and a sucralfate suspension", Eur. J. Biopharm., vol. 39(2) (1991) pp. 70-74.

Laine et al., "Prospective study of fluconazole suspension for the treatment of oesophageal candidiasis in patients with AIDS", Aliment Pharmacol Ther. 1995:9, pp. 553-556.

Martins et al., "Fluconazole suspension for oropharyngeal candidiasis unresponsive to tablets", Annals of Internal Medicine, vol. 126, No. 4 (Feb. 15, 1997) pp. 332-333.

Potts et al., "In vivo determination of the oesophageal retention of smart hydrogel™", Proceedings International Symp. Control. Rel. Bioact. Mater., 24 (1997), Controlled Release Society, Inc., pp. 335-336, 3 pages total.

Richardson et al., "Oesophageal bioadhesion of sodium alginate suspensions: particle swelling and mucosal retention", European Journal of Pharmaceutical Sciences, vol. 23 (2004) pp. 49-56, available online Jul. 10, 2004.

Smart et al., "The retention of 14C-labelled poly (acrylic acids) on gastric and oesophageal mucosa: an in vitro study", European Journal of Pharmaceutica Sciences, vol. 20 (2003) pp. 83-90.

Tang et al., "Bioadhesive oesophageal bandages: protection against acid and pepsin injury", International Journal of Pharmaceutics, vol. 292 (2005) pp. 169-177.

Wise et al., "Regional differences in oesophageal motor function", Neurogastroenterol Motil Blackwell Publishing Ltd. (2004) 16, pp. 31-37.

Young et al., "A novel in-vitro apparatus for evaluating the mucoadhesion of liquid and semi-solid formulations", J. Pharm. Pharmacol. (1998), 50 (Supplement), p. 167, 1 page total.

Zhang et al., "A bioadhesive formulation for the delivery of antifungal agents to the oesophagus", JJP (2004), 56 (Supplement), S-16, 1 page total.

Aceves et al., "Prospective Analysis of an Abdominal Symptom Scoring Tool's Efficacy in the Clinical Distinction of Pediatric Eosinophilic Esophagitis from Gastroesophageal Reflux Disease," J. Allergy Clin. Immunol. Feb. 2008, S70 Abstracts No. 270.

Aceves, S et al., "Distinguishing Eosinophilic Esophagitis in pediatric patients: clinical, endoscopic, and histologic features of an emerging disorder," Journal of Clinical Gastroenterology 2006; 41(3):252-6.

Aceves, SS et al. "Topical viscous budesonide suspension for treatment of eosinophilic esophagitis," J. Allergy Clin. Immunol. 2005; 116(3):705-6.

Aceves, SS et al., "Oral viscous budesonide: a potential new therapy for eosinophilic esophagitis in children," Amer. Journal of Gastroenterology 2007; 102:1-9.

Ashorn et al., "The Natural Course of Gastroesophageal Reflux Disease in Children," Scand. J. Gastroenterol. 37(6):638-641 (2002).

Blanchard et al., "Eotaxin-3 and a uniquely conserved gene-expression profile in eosinophilic esophagitis," J. Clin Invest. 116(2):536-547 (2006).

Bogaart, H.C.A. et al., "Viscosity Is Not a Parameter of Postdeglutitve Pharyngeal Residue: Quantification and Analysis with Scintigraphy," Dysphagia 22:145-149 (2007).

Bonis, P. et al., "Eosinophilic esophagitis," downloaded from the internet on Aug. 7, 2008 at http://www.uptodate.com/online/content/topic.do?topicKey=eso_dis/11927&view=print.

Budin, C et al. "Eosinophilic esophagitis: 3 case reports," Gastroenterol. Clin. Biol. 2005; 29:73-5.

Campieri et al., "Oral budesonide is as effective as oral prednisolone in active Crohn's disease," Gut 41:209-214 (1997).

Caro, J.J. et al., "Healing and relapse rates in gastroesophageal reflux disease treated with the newer proton-pump inhibitors lansoprazole, rabeprazole, and pantoprazole compared with omeprazole, ranitidine, and placebo: evidence from randomized clinical trials," Clin. Thera. 23(7):998-1017 (2001).

Cherian S et al., "Rapidly increasing prevalence of eosinophilic oesophagitis in Western Australia," Arch. Dis. Child 2006; 91:1000-4.

Cheung, K M et al., "Esophageal eosinophilia in children with dysphagia," J. Pediatr. Gastroenterol. Nutr. 2003;37:498-503.

Collaud, S. et al., "Clinical evaluation of bioadhesive hydrogels for topical delivery of hexylaminolevulinate to Barrett's esophagus," J. Controlled Release 123:203-210 (2007).

Croese J et al., "Clinical and endoscopic features of eosinophilic esophagitis in adults," Gastrointest. Endosc. 2003; 58(4):516-22.

Desai T K et al., "Association of eosinophilic inflammation with esophageal food impaction in adults," Gastrointest. Endosc. 2005; 61(7):795-801.

Dohil R et al., "The evaluation and treatment of gastrointestinal disease in children with cystinos is receiving cysteamine," J. Pediatr. 2003; 14:224-30.

Faubion W A, Jr. et al., "Treatment of eosinophilic esophagitis with inhaled corticosteroids," J. Pediatr. Gastroenterol. Nutr. 1998; 27(1):90-3, downloaded from the internet on Jul. 30, 2007 at http://gateway.tx.ovid.com.proxy.lib.mcw.edu/gw1/ovidweb.cgi.

Fogg M I et al., "Pollen and eosinophilic esophagitis," J. Allergy Clin. Immunol. 2003; 112:796-7.

Fox V L et al., "Eosinophilic esophagitis: it's not just kid's stuff," Gastrointest. Endosc. 2002; pp. 1-15.

Furuta, GT et al., "Eosiniophilic esophagitis in children and adults: A systematic review and consensus recommendations for diagnosis and treatment," Gastroenterology 2007; 133:1342-63.

Garrett J K et al., "Anti-interleukin-5 (mepolizumab) therapy for hypereosinophilic syndromes," J. Allergy Clin. Immunol. 2004; 113:115-9.

GB0911779.7 Search Report dated Aug. 18, 2009, 4 pages.

Gilani, K. et al., "Aerosolisation properties of disodium cromoglycate microparticles spray dried from different water to ethanol ratio," JPP S6(Suppl.):Abstract 043 (2004).

Guajardo J R et al., "Eosinophil-associated gastrointestinal disorders: a world-wide-web based registry," J. Pediatr. 2002; 141:576-81.

Hanauer, S.B., "Therapy Update: New steroids for IBD: progress report," Gut 51:182-183 (2002).

Hellers, et al., "Oral Budesonide for Prevention of Postsurgical Recurrence in Crohn's Disease," Gastroenterol. 116:294-300 (1999).

Honkanen, O. et al., "Bioavailibility and in vitro oesophageal sticking tendency of hydroxypropyl methylcellulose capsul formulations and corresponding gelatine capsul formulations," Eur. J. Pharm. Sci. 15:479-488 (2002).

Ishibashi, H. et al., "Oral administration of itraconazole solution has superior efficacy in experimental oral and oesophageal candidiasis in mice than its intragastric administration," J. Antimicrobial Chemotherapy 59:317-320 (2007).

Kagalwalla A F et al., "Effect of six-food elimination diet on clinical and histologic outcomes in eosinophilic esophagitis," Clin. Gastroenterol. Hepatol. 2006; 4:1097-102.

Karnam U. et al., "Effectiveness of oral budesonide suspension in adult patients with eosinophilic esophagitis," 1 page, downloaded from the internet on May 13, 2008 at http://download.abstractcentral.com/ddw2008/myddw2008/S1974.html.

Kelly K J et al., "Eosinophilic esophagitis attributed to gastroesophageal reflux: improvement with an amino acid-based formula," Gastroenterology 1995; 109: 1503-12.

Khan et al., "Esoinophilic Gastroenteritis. Epidemiology, Diagnosis and Management," Pediatr. Drugs 4(9):563-570 (2002).

Konikoff et al., "A Randomized, Double-Blind, Placebo-Controlled Trial of Fluticasone Propionate for Pediatric Eosinophilic Esophagitis," Gastroenterol. 131:1381-1391 (2006).

Li, W. et al., "Clinical and endoscopic features of Chinese reflux esophagitis patients," World J. Gastroenterol, Mar. 28, 2008, 14(12):1866-71.

Liacouras C A et al., "Eosinophilic esophagitis," Curr. Opin. Pediatr. 2004; 16:560-6.

Liacouras C A et al., "Eosinophilic esophagitis: a 10-year experience in 381 children," Clin. Gastroenterol. Hepatol. 2005; 3:1198-206.

Liacouras C A et al., "Primary eosinophilic esophagitis in children: successful treatment with oral corticosteroids," J. Pediatr. Gastroenterol. Nutr. 1998; 26(4):380-5.

Liacouras C A., "Eosinophilic esophagitis: treatment in 2005," Curr. Opin. Gastroenterol. 2006; 22:147-152.

Markowitz J E et al., "Elemental diet is an effective treatment for eosinophilic esophagitis in children and adolescents," Am. J. Gastroenterol. 2003; 98(4):777-82.

Mishra A et al., "An etiological role for aeroallergens and eosinophils in experimental esophagitis," J. Clin. Invest. 2001; 107(1):83-90.

Mueller S et al., "Eosinophil infiltration and degranulation in oesophageal mucosa from adult patients with eosinophilic oesophagitis: a retrospective comparative study on pathologic biopsy," J. Clin. Pathol. 2006; 59:1175-80.

Newman, S.P. et al., "New developments in radionuclide imaging for assessing drug delivery in man," Eur. J. Pharma. Sci. 18:19-22 (2003).

Nicolazzo, JA et al., "Buccal penetration enhancers—how do they really work?" J. Controlled Release 2005; 105:1-15.

Noel R J et al., "Clinical and immunopathologic effects of swallowed fluticasone for eosinophilic esophagitis," Clin. Gastroenterol. Hepatol. 2004; 2:568-75.

Noel R J et al., "Eosinophilic esophagitis," N. Engl. J. Med. 2004; 351:940-1.

Oliviera, C. et al., "Eosinophilic esophagitis and intermediate esophagitis after tracheoesophageal fistula repair: a case series," J. Ped. Surg. 43:810-814 (2008).

Orenstein S R et al., "The spectrum of pediatric eosinophilic esophagitis beyond infancy: a clinical series of 30 children," Am. J. Gastroenterol. 2000; 95(6):1422-30.

Parfitt J R et al., "Eosinophilic esophagitis in adults: distinguishing features from gastroesophageal reflux disease: a study of 41 patients," Mod. Pathol. 2006; 19:90-6.

PCT/US2008/012712 Search Report dated Jun. 25, 2009, 4 pages.

PCT/US2008/012780 Search Report dated Jun. 25, 2009, 4 pages.

PCT/US2008/012781 Search Report dated Jun. 25, 2009, 4 pages.

PCT/US2008/012783 Search Report dated Jun. 16, 2009, 4 pages.

PCT/US2008/083288 Search Report dated May 18, 2009, 4 pages.

PCT/US2008/083290 Search Report dated Jul. 15, 2009, 6 pages.

PCT/US2009/041316 Search Report and Written Opinion dated Oct. 30, 2009, 13 pages.

Plaza-Martin, AM et al., "Polysensitization to aeroallergens and food in eosinophilic esophagitis in a pediatric population," Alergol. Immunopathol. 2007; 35(1):35-7.

Potter J W et al., "Eosinophilic esophagitis in adults: an emerging problem with unique esophageal features," Gastrointest. Endosc. 2004; 59(3):355-61.

Ravelli A M et al., "Dilated Intercellular Spaces: A Major Morphological Feature of Esophagitis," J. Pediatr. Gastroenterol. Nutr. 2006; 42:510-515.

Remedios M et al., "Eosinophilic esophagitis in adults: clinical, endoscopic, histologic findings, and response to treatment with fluticasone propionate," Gastrointest. Endosc. 2006; 63(1):3-12.

Rothenberg M E, et al., "Pathogenesis and clinical features of eosinophilic esophagitis," J. Allergy Clin. Immunol. 2001; 108:891-4.

Rothenberg M E., "Eosinophilic gastrointestinal disorders (EGID)," J. Allergy Clin. Immunol. 2004; 113:11-28.

Rowe et al., "Handbook of Pharmaceutical Excipients," Pharmaceutical Press, Jan. 1, 2006, pp. 442-445.

Ruchelli E et al., "Severity of esophageal eosinophilia predicts response to conventional gastroesophageal reflux therapy," Pediatr. Dev. Pathol. 1999; 2:15-8.

Sant'Anna A M et al., "Eosinophilic Esophagitis in Children: Symptoms, Histology and pH Probe Results," J. Pediatr. Gastroenterol. Nutr. 2004; 39:373-377.

Shah, A. and Hirano, I., "Treatment of Eosinophilic Esophagitis: Drugs, Diet, or Dilation?" Curr. Gastroent. Reports 9:181-188 (2007).

Sharpe, S.A. et al., "Comparison of the Flow Properties of Aqueous Suspension Corticosteroid Nasal Sprays Under Differing Sampling Conditions," Drug Dev. Industrial Pharmacy 29(9):1005-1012 (2003).

Sicherer, S.H., "Clinical Aspects of Gastrointestinal Food Allergy in Childhood," Pediatr. 111(6):1608-1616 (2003), downloaded from the internet on Sep. 28, 20009 at www.pediatrics.org.

Spergel J M et al., "The use of skin prick tests and patch tests to identify causative foods in eosinophilic esophagitis," J. Allergy Clin. Immunol. 2002; 109:363-8.

Spergel J M et al., "Treatment of eosinophilic esophagitis with specific food elimination diet directed by a combination of skin prick and patch tests," Ann. Allergy Asthma Immunol. 2005; 95:336-43.

Spergel JM., "Eosinophilic esophagitis in adults and children: evidence for a food allergy component in many patients," Curr. Opin. Allergy Clin. Immunol. 2007; 7:274-8.

Steiner S J et al., "Correlation between number of eosinophils and reflux index on same day esophageal biopsy and 24 hour esophageal pH monitoring," Am. J. Gastroenterol. 2004; 99:801-5.

Steiner S J et al., "Severity of Basal Cell Hyperplasia Differs in Reflux Versus Eosinophilic Esophagitis," J. Pediatr. Gastroenterol. Nutr. 2006; 42:506-509.

Straumann A and Simon H U, "Eosinophilic esophagitis: escalating epidemiology?" J. Allergy Clin. Immunol. 2005; 115:418-9.

Straumann A et al., "Natural history of primary eosinophilic esophagitis: a follow-up of 30 adult patients for up to 11.5 years," Gastroenterology 2003; 125:1660-9.

Suarez, C.L. et al., "Caustic esophagitis in children," Anales Espanoles de Pediatria, Mar. 1992, 36(3):205-207, Abstract, 1 page.

Teitelbaum J E et al., "Eosinophilic esophagitis in children: immunopathological analysis and response to fluticasone propionate," Gastroenterology 2002; 122:1216-25.

Varum, F.J.O. et al., "Mucoadhesion and the Gastrointestinal Tract," Critical Reviews Ther. Drug Carrier Systems 25(3):207-258 (2008).

Watts, et al., "TARGIT™ technology coated starch capsules for site-specific drug delivery into the lower gastrointestinal tract," Exp. Op. Drug Delivery 2(1):159-167 (2005), Abstract, 1 page.

Zhang, L. et al., "Strategies and therapeutic opportunities for the delivery of drugs to the esophagus," Critical Reviews Ther. Drug Carrier Systems 25(3):259-304 (2008).

International Preliminary Report on Patentability dated Feb. 22, 2011 for International PCT Application No. PCT/US2008/083290, 7 pages.

Martin, Alfred, "Micromeritics", Physical Pharmacy, 4th edition, p. 423, published by Lea & Febiger, 1993.

* cited by examiner

Figure 1. Pretreatment distal esophageal biopsy showing marked basal zone hyperplasia (white arrow), numerous intraepithelial eosinophils (black arrow) with a few degranulated eosinophils, intercellular edema and fibrosis of the lamina propria (Hematoxylin & eosin, original magnification x 125; inset x 500). Basal zone hyperplasia is reported when basal zone cells extend towards the luminal surface of the epithelium (>25% of epithelial thickness).

Figure 2. Post-treatment distal esophageal biopsy showing normalization. Note absence of eosinophils and intercellular edema (Hematoxylin & eosin, ,original magnification x 125, inset x 500).

Figure 3. Distal esophageal image of patient with eosinophilic esophagitis (Olympus P160 endoscope) showing pallor, lichenification of the mucosa with linear furrowing (arrow). Following treatment with viscous budesonide, the esophagus appears normal (lower).

VISCOUS BUDESONIDE FOR THE TREATMENT OF INFLAMMATORY DISEASES OF THE GASTROINTESTINAL TRACT

PRIORITY

Priority is claimed to U.S. Provisional Application Ser. No. 60/735,340, filed Nov. 12, 2005, and entitled Viscous Budesonide for the Treatment of Inflammatory Diseases of the Gastrointestinal Tract which is referred to and incorporated herein by reference in its entirety.

FIELD OF THE INVENTION

The invention is in general directed to methods and pharmaceutical compositions for preventing or alleviating the symptoms of and inflammation associated with inflammatory diseases involving the esophagus.

BACKGROUND

Eosinophilic esophagitis (EE) is an emerging, and fast-growing disorder characterized by high levels of eosinophils in the esophagus, as well as basal zone hyperplasia. EE is thought to be provoked, in at least a subset of patients, by food allergies or airborne allergen exposure (Rothenberg M E. Eosinophilic gastrointestinal disorders. J Allergy Clin Immunol. 2004; 113:11-28; Fogg M J, Ruchelli E, Spergel J M. Pollen and eosinophilic esophagitis J Allergy Clin Immunol 2003; 112:796-7; refs 1-5). In parallel with other atopic disorders, the incidence of EE appears to be increasing (Noel R J, Putnam P E, Rothenberg M E. Eosinophilic esophagitis. N Eng J Med 2004; 351:940-1; Straumann A, Simon H U. Eosinophilic esophagitis: escalating epidemiology? J Allergy Clin Immunol 2005; 115:418-9.). The disorder may present with reflux-like symptoms, pain and dysphagia. Symptoms of EE include, for example, abdominal pain, chest pain, choking, difficulty swallowing, failure to thrive, nausea, reflux not relieved by standard anti-flux therapy, skin rash or hives, vomiting, and weight loss. In one series, 15% of EE patients had concurrent developmentaldelay (Garrett J K, Jameson S C, Thomson B, Collins M H, Wagoner L E, Freese, D K, et al. Anti-interleukin-5 (mepolizumab) therapy for hypereosinophilic syndromes. J Allergy Clin Immunol. 2004; 113:115-9.). Diagnosis is often made in young children and depends on the finding of 20 or more to 24 or more eosinophils per high power field (eos/hpf) within esophageal mucosal biopsies. (refs 6-12).

Although EE is becoming more frequently diagnosed throughout developing countries (7, 8, 13-16) many aspects of the disease remain unclear including its etiology, natural history and optimal therapy. Symptoms of EE often mimic those of GER and include vomiting, dysphagia, pain and food impaction (8, 14, 17-20). However, treatment of EE and GERD differ and it is important to distinguish between them, particularly as untreated EE may be associated with esophageal narrowing in 10-30% of cases (14, 18, 20, 21).

Long term systemic steroid therapy can result in significant secondary side effects on growth and bone development, therefore topical steroid formulations are often used to treat EE and potentially other inflammatory gastrointestinal diseases and conditions involving the esophagus. Although treatment with anti-IL-5 monoclonal antibody has been reported to be successful in EE, this therapy is currently not approved for use in children (Guajardo J R, Plotnick L M, Fende J M, Collins M H, Putnam P E, Rothenberg M E. Eosinophil-associated gastrointestinal disorders: a worldwide web based registry. J Pediatr. 2002; 141:576-81.).

Current treatments include elimination diets (22,23), and elemental formulas (2, 24). Identifying true inciting food allergens can be difficult and elemental formulas are often unpalatable, thereby making dietary interventions complicated (1, 22). Systemic corticosteroids and swallowed topical steroids, such as fluticasone proprionate (Flovent™) administered through metered-dose inhaler (MDI), have been shown to induce and maintain low esophageal eosinophil levels (25-30). In one method, for example, a fluticasone metered dose inhaler (MDI) is puffed into the oropharynx and swallowed (Teitelbaum, J E, Fox, V L, Twarog F J, Nurko S, Ntonioli D, Gleich G, Badizadegan K, Furuta G T. Eosinophilic esophagitis in children: immunopathological analysis and response to fluticasone propionate. Gastroenterology. 2002; 122:1216-25.). This puff and swallow technique is often difficult for patients, especially smaller children, and especially children with developmental delays, to perform efficiently. This results in a less than effective dose of the topical steroid being delivered to the esophagus.

Systemic corticosteroids are also used to treat inflammatory bowel diseases that are manifested in the esophagus, including, for example, Crohn's disease or allergic gastroenteritis. These drugs are also used to treat inflammatory esophageal conditions other than EE, such as, for example, esophageal inflammation secondary to caustic/irritant ingestion, persistent/recurrent esophageal strictures of any cause and including caustic/irritant ingestion, pill-induced esophagitis (caused when a pill becomes lodged in the esophagus during swallowing, followed by inflammation that persists after the pill is removed), systemic diseases, congenital diseases, or post-surgery inflammation. It is often difficult to deliver an effective dose of corticosteroid to the targeted area of the esophagus. Other inflammatory bowel diseases in which steroid therapy is useful include, for example, Crohn's disease, which may affect any part of the gastrointestinal tract, from the mouth to the anus.

Budesonide, 16,17-(butylidenebis(oxy))-11,21-dihydroxy-, (11-β,16-α)-pregna-1,4-diene-3,20-dione, is a corticosteroid sometimes used in inhaled form to treat inflammatory diseases or conditions such as asthma, or nasal inflammation, or in other forms, such as by oral delivery or enema, to treat other lower inflammatory lower gastrointestinal diseases or conditions such as Crohn's disease.

There is a need for novel methods for preventing and alleviating inflammatory diseases and conditions involving the esophagus. A liquid, long-acting topical corticosteroid preparation is needed.

SUMMARY

Provided herein are methods for preventing and alleviating any chronic inflammatory or malignant state that involves the esophagus and responds to steroid therapy. The methods of the present invention are useful, for example, for preventing and alleviating the symptoms and inflammation of eosinophilic esophagitis, inflammatory bowel diseases involving the esophagus, Crohn's disease, esophageal inflammation secondary to caustic/irritant ingestion, persistent/recurrent esophageal strictures of any cause and including caustic/irritant ingestion, pill-induced esophagitis, systemic diseases, congenital diseases, Epidermolysis bullosa, and post-surgery inflammation. The present methods are also useful for preventing or alleviating symptoms and inflammation associated with other diseases or conditions of the gastrointestinal tract, for example, the upper gastrointestinal tract, where it is beneficial to target a particular target site, rather than provide systemic therapy. Also provided herein are pharmaceutical compositions useful in the methods of the present application.

Thus, in one embodiment is provided a method of preventing or alleviating esophageal inflammation in an individual comprising orally administering to said individual a corticosteroid in association with at least one excipient to increase the viscosity of the composition. In certain embodiments, the viscosity of the composition is about that of a suspension prepared by adding about 5 to about 15 grams of sucralose to 4 ml of water, or about 10 to about 12 grams of sucralose to 4 ml of water, wherein the viscosity is measured at 25 degrees Celsius. In certain aspects, the corticosteroid is a topical corticosteroid, such as, for example, Budesonide. In some embodiments, the individual has eosinophilic esophagitis. The individual may, for example, have been diagnosed with a disease or condition selected from the group consisting of eosinophilic esophagitis, inflammatory bowel diseases involving the esophagus, Crohn's disease, esophageal inflammation secondary to caustic/irritant ingestion, persistent/recurrent esophageal strictures of any cause and including caustic/irritant ingestion, pill-induced esophagitis, systemic diseases, congenital diseases, and post-surgery inflammation.

Although the methods of the invention may be used to prevent or alleviate esophageal inflammation in a mammal, for example a human, of any age, in certain examples, the individual is a child, for example, a child less than 16, 15, 14, 13, 12, 11, 10, 9, 8, 7, 6, 5, 4, 3, 2, or 1 years old.

Also provided in the present invention is a pharmaceutical composition comprising a corticosteroid and a viscosity-increasing excipient, for example, a topical corticosteroid, such as, for example, Budesonide. The pharmaceutical composition may be, for example, in liquid form. Also provided are pharmaceutical compositions comprising a corticosteroid, for example a topical corticosteroid, such as, for example, Budesonide, in the form of a dissolving tablet, a dissolving wafer, a capsule, or a gel capsule. In certain embodiments, these tablets, wafers, and capsules are formulated with at least one excipient to deliver a viscous form of the corticosteroid to the esophagus.

The excipient may be, for example, selected from the group consisting of lactose, sucrose, sucralose, mannitol, sorbitol, honey, maize starch, wheat starch, rice starch, potato starch, gelatin, gum tragacanth, methyl cellulose, hydroxypropylmethyl-cellulose, sodium carboxymethyl-cellulose (CMC), and polyvinylpyrrolidone (PVP: povidone). The excipient may be, for example, selected from the group consisting of lactose, sucrose, sucralose, mannitol, sorbitol, honey, maize starch, wheat starch, rice starch, potato starch, gelatin, gum tragacanth, methyl cellulose, hydroxypropylmethyl-cellulose, sodium carboxymethyl-cellulose (CMC), and polyvinylpyrrolidone (PVP: povidone). In certain illustrative examples, the excipient is sucralose.

The pharmaceutical composition in certain embodiments comprises a therapeutically effective amount of corticosteroid to prevent or alleviate esophageal inflammation. In certain embodiments, 1-2 mg or 2-3 mg or corticosteroid per day is administered to said individual.

DETAILED DESCRIPTION OF THE DRAWINGS

DESCRIPTION

Abbreviations: EE: Eosinophilic Esophagitis; MDI: Metered Dose Inhaler; hpf: high powered field; eos: eosinophil.

Provided herein are methods and pharmaceutical compositions for preventing or alleviating the symptoms of and inflammation associated with inflammatory diseases involving the esophagus.

It has been found that by administering Budesonide in oral form, in a formulation with increased fluid viscosity, that the corticosteroid was delivered to the esophagus in an effective dose to reduce the inflammation of the esophagus. In the treatment of more than 40 patients, this treatment was found to be effective in targeting inflammation within the esophagus. Specific examples of two patients, both children, are presented in Examples 1 and 2. A viscous oral suspension of budesonide improved symptoms, resolved endoscopic abnormalities, and markedly reduced or eliminated esophageal eosinophils in two patients unable to utilize a metered dose inhaler with puff and swallow technique. Although this therapy is particularly beneficial to children in that they often have the most difficulty using the puff and swallow technique, the methods of the present invention may also be used for individuals of any age. By "individual" is meant any animal, for example, a mammal, or, for example, a human, including, for example, patients in need of treatment.

Diseases

Diseases or conditions that may be treated, prevented, or exhibit an alleviation of symptoms according to the present invention include any disease or condition that involves esophageal inflammation. This includes, for example, any chronic inflammatory or malignant state that involves the esophagus and responds to steroid therapy. The methods of the present invention are useful, for example, for preventing and alleviating the symptoms of eosinophilic esophagitis, inflammatory bowel diseases involving the esophagus, Crohn's disease, acute esophageal inflammation secondary to caustic/irritant ingestion, persistent/recurrent esophageal strictures secondary to caustic/irritant, conditions due to ingestion, systemic diseases, congenital diseases, and post-surgery inflammation.

It will be appreciated by those skilled in the art that reference herein to treatment extends to prophylaxis as well as the treatment of inflammation or other symptoms.

Compounds

Compounds useful in the present invention include topical steroids that may be used to treat inflammatory gastrointestinal conditions, including, for example, Budesonide.

Formulation

While the compositions of the present invention will typically be used in therapy for human patients, they may also be used in veterinary medicine to treat similar or identical diseases. The compositions may, for example, be used to treat mammals, including, but not limited to, primates and domesticated mammals. The compositions may, for example be used to treat herbivores. The compositions of the present invention include geometric and optical isomers.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

Liquid suspensions of the present invention include, for example, those prepared by adding about 5 to about 25 grams of sucralose, or about 7 to about 20 grams of sucralose, or about 5 to about 15 grams of sucralose, or about or about 7 to about 15 grams of sucralose, or about 8 to about 12 grams of sucralose, or about 10 to about 11 grams of sucralose, or 4, 5, 6, 7, 8, 9, 10, 11, 12, 13, 14, 15, 16, 17, 18, 19, 20, 21, 22, 23, 24, or 25 grams of sucralose, added to 4 ml of Budesonide, such as that obtained from a Budesonide respule, or larger volumes having the same ratios of sucralose to Budesonide.

The exact dosage will depend upon the route of administration, the form in which the composition is administered, the subject to be treated, the age, body weight/height of the subject to be treated, and the preference and experience of the attending physician. The optimal concentration of the corticosteroid in the composition will necessarily depend upon the specific corticosteroid used, the characteristics of the patient, and the nature of the inflammationfor which the treatment is sought. These factors can be determined by those of skill in the medical and pharmaceutical arts in view of the present disclosure. Generally, a therapeutically effective dose is desired. A therapeutically effective dose refers to that amount of the corticosteroid that results in a degree of amelioration of symptoms and inflammation relative to the status of such symptoms prior to treatment. The dosage forms containing effective amounts are within the bounds of routine experimentation and therefore, well within the scope of the instant invention. In general however, a suitable dose may be in the range of from about 10 to 400 ug/kg of body weight per day, or for example, in the range of 20 to 300 ug/kg per day, or for example in the range of 30 to 200 ug/kg per day, or for example in the range of 30 to 100 ug/kg per day, or for example in the range of 35 to 100 ug/kg per day, or for example in the range of 30-50 ug/kg per day, or for example in the range of 40-100 ug/kg/day, or for example in the range of 40-60 ug/kg/day, or in an illustrative embodiment in the range of 35-60 ug/kg/day. In an illustrative embodiment, the dosage is provided in a sufficient volume to allow the composition to reach the esophagus in an effective amount. In general, in a liquid dose, the dosage may be provided in, for example 5-50 ml, or for example 5-40 ml, or for example 5-30 ml, or for example 5-25 ml, or for example 10-25 ml, or, in an illustrative example 5-15 ml. Those of ordinary skill in the art would be able to determine an appropriate palatable dosage that is of sufficient volume to deliver a therapeutically effective amount of corticosteroid to the esophagus. For example, those of ordinary skill in the art would be able to determine an appropriate palatable dosage that is of sufficient volume to coat the esophagus, in an illustrative embodiment, the volume would be sufficient to coat the lower esophagus. The composition may be delivered, for example, once a day, every other day, three times a week, or twice a week. The dosage may, for example, be divided into multiple doses throughout the day, or be provided, for example, in four, three, two, or one dose a day. In one illustrative example, the dose is provided once a day.

In other illustrative embodiments of the invention, the Budesonide is provided in the form of a lozenge which may be dissolved in the mouth, thus reaching and coating the esophagus. The lozenge or other similar tablet, capsule, or other solid, wold dissolve rapidly in the mouth or esophagus to produce a solution that can then coat the esophagus. Or, for children or other patients that may have difficulty with a dissolving lozenge, the lozenge may be ground or otherwise dissolved in a small volume of water or other pharmaceutically suitable liquid, for example, reaching a total volume presented in embodiments herein. In other illustrative embodiments of the invention, the Budesonide is provided in the form of a tablet, a capsule, or, for example a gel capsule, designed for slow release and delivery to the esophagus.

Initial treatment may continue, for example, for about 3 days to 2 weeks for an acute condition, or about 4 weeks to about 16 weeks for a chronic condition, or about 8 weeks to about 12 weeks for a chronic condition. Longer therapy may also be needed, such as, for example, therapy similar to chronic therapy for persistent asthma. Patients may, for example, be treated for up to 6 months, or up to one year. Maintenance treatment can last up to or longer than one year. Patients may be treated on a maintenance basis or on an as needed basis during a problematic episode, depending on the severity of the condition. Patients can also be treated on a rotating treatment basis, where treatment is provided for a period of time and then the patient is taken off of the drug for a period before treatment resumes again. When off the drug, the patient may be given no treatment, treatment with another medication, or treatment with a reduced dosage. Or, patients may be given treatment with a higher dose of the composition until a desired reduced disease state is achieved, and then continued on a lower dose of the composition.

The compositions of the present invention may include pharmaceutically acceptable salts. Pharmaceutically acceptable salts are generally well known to those of ordinary skill in the art and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycolylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy (20.sup.th ed.) Lippincott, Williams & Wilkins (2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, the compositions may be formulated into liquid or solid dosage forms and administered systemically or locally. The agents may be delivered, for example, in a timed- or sustained-low release form as is known to those skilled in the art. Techniques for formulation and administration may be found in Remington: The Science and Practice of Pharmacy (20th ed.) Lippincott, Williams & Wilkins (2000).

In addition to the active ingredients, these pharmaceutical compositions may contain suitable pharmaceutically acceptable carriers comprising excipients and auxiliaries. Use of pharmaceutically acceptable carriers to formulate the corticosteroids herein disclosed for the practice of the invention into dosages suitable for systemic administration is within the scope of the invention. The corticosteroids may be formulated readily using pharmaceutically acceptable carriers well known in the art into dosages suitable for oral administration. Such carriers enable the compositions of the invention to be formulated as tablets, pills, dragees, capsules, liquids, gels, syrups, slurries, suspensions and the like, for oral ingestion by a patient to be treated.

Pharmaceutical preparations for oral use may be obtained by combining the corticosteroids with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, sucralose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate. For dissolving tablets, appropriate excipients include those that increase the resulting liquid viscosity of the dissolved tablet, enabling it to reach the esophagus, for example, to coat the esophagus. Appropriate excipients may also, for example, include those that render the dissolving tablet palatable.

For liquid form, appropriate excipients may be added to increase the liquid viscosity of the liquid composition. Appropriate excipients may also, for example, include those that render the liquid composition palatable. Excipients may include, for example, either sugars, including lactose, sucrose, sucralose, mannitol, or sorbitol; honey; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone).

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active corticosteroid doses.

Pharmaceutical preparations that may be used orally also include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the corticosteroids may be dissolved or suspended in suitable liquids, such as fatty oils, liquid paraffin, or liquid polyethylene glycols (PEGs). In addition, stabilizers may be added.

In one illustrative embodiment, the corticosteroid of the composition has a low bioavailability, so that much of it will remain in the gastrointestinal tract, for example, in the esophagus. This may result in decreased systemic side effects and complications, allowing patients with chronic conditions to receive treatment for longer periods of time.

Viscosity

Excipients, such as, for example, those listed herein, may be included in the composition to increase the viscosity of the delivered composition. The liquid viscosity may be increased in the oral form, or the excipient may increase the viscosity of the dissolved form of a tablet. Those of ordinary skill in the art will recognize that the viscosity should be at a level that is sufficient to deliver an effective amount of the composition to the esophagus, for example, in an amount that may coat the esophagus. Also, the viscosity should be at a level that may be given orally, thus not so thick that it is either too difficult to swallow, causes gagging, or is unpalatable. Those of ordinary skill in the art may determine the viscosity of the compositions provided in the Examples, and may thus determine appropriate ranges. One method of determining whether the composition is sufficiently viscous is by determining whether the inflammation, or eosinophilic infiltration, of the esophagus is reduced after treatment with the corticosteroid.

Viscosity can be determined by any method that will measure the resistance to shear offered by the substance or preparation. Many viscometers are available to those in the pharmaceutical field, and include those built by, for example, Brookfield.

Viscosity may be, for example, measured at room temperature, at about 20-25 degrees Celsius, or at about 37 degrees Celsius to mimic body temperature. The viscosity of a liquid generally decreases as the temperature is raised. In some embodiments of the invention, the viscosity is about the viscosity of about 5 to about 25 grams of sucralose, or about 7 to about 20 grams of sucralose, or about 5 to about 15 grams of sucralose, or about or about 7 to about 15 grams of sucralose, or about 8 to about 12 grams of sucralose, or about 10 to about 11 grams of sucralose, added to 4 ml water, at 25 degrees Celsius. In an illustrative embodiment, the viscosity is about the viscosity of 10 grams of sucralose added to 4 ml of water, at 25 degrees Celsius. In other embodiments, the viscosity is about the viscosity of 5 to 20 grams of sucralose in 8 ml total liquid volume, at 25 degrees Celsius. In other embodiments, the viscosity is about the viscosity of 5 to 15 grams of sucralose in an 8 ml total liquid volume, at room temperature. In other embodiments, the viscosity is about the viscosity of 8 to 12 grams of sucralose in an 8 ml total liquid volume at 25 degrees Celsius. In some embodiments, the viscosity is between that of about a fruit nectar and commercial honey, where the viscosity is measured at 25 degrees Celsius.

Example 1

Patient 1 was a 6-year-old male with a history of abdominal pain, failure to thrive, and vomiting since infancy, and developmental delay with isolated EE diagnosed in 2001. His allergic history was significant for allergic rhinitis secondary to cat, dog, and dust mite exposure as well as positive Pharmacia CAP radioallergosorbent testing for fish and milk. Following upper gastrointestinal endoscopy (EGD) with esophageal biopsies demonstrating a maximum eosinophil count of 60 per high-powered field (hpf at 400× magnification) he was diagnosed with EE and treated with oral corticosteroid (prednisone 0.5 mg per kg daily) for one month. This resulted in resolution of esophageal eosinophilia with a maximum of 2 eosinophils per hpf on repeat EGD with biopsy. He was subsequently treated with omeprazole (Prilosec®) 10 mg twice daily and fluticasone (Flovent®) 220 ug twice daily as topical esophageal therapy but repeat EGD with biopsy after 6 months demonstrated a maximum eosinophil count of 50 per hpf. His therapeutic regimen was changed to elemental formula and fluticasone but repeat EGD with biopsy demonstrated persistent esophageal eosinophils with a maximal eosinophil count of 74 per hpf accompanied by basal zone hyperplasia. He was referred to Children's Hospital Eosinophilic Gastrointestinal Disorders clinic for further management of EE recalcitrant to usual therapy. At the time of his referral, he continued to have vomiting and poor weight gain and his mother reported significant difficulty with the puff and swallow technique. He was placed on a regimen of twice daily oral budesonide suspension (Pulmicort®) 500 micrograms (4 ml) mixed with about 10 packets (1 gram each) sucralose, (Splenda®), a non-absorbed sugar in order to increase fluid viscosity to be swallowed twice daily. The total volume of the preparation was about 7 to 8 ml. Following 3 months of therapy, repeat EGD showed a normal esophagus and biopsies demonstrated complete resolution of both esophageal eosinophils and basal zone hyperplasia. In addition, his abdominal pain and vomiting resolved, resulting in increased appetite with documented weight gain. Eight am cortisol was 13.2 mcg/dL (normal range for age 3-15 mcg/dL) after four months of therapy.

Example 2

Patient 2 was a 5-year-old girl with a history of developmental delay, abdominal pain, and RAST positivity for milk, egg, and wheat. EGD showed a normal esophagus but histopathology of biopsies demonstrated maximal eosinophil counts of 40 per hpf and basal zone hyperplasia. She was placed on a hydrolyzed formula containing milk protein (Peptamen Jr®), omeprazole 10 mg twice daily and oral cromolyn (Gastrocrom®) 100 mg four times daily. Following 12 months of therapy, repeat EGD demonstrated a pale, furrowed esophagus with maximum eosinophil counts of 94, 65, and 90 per hpf and diffuse basal zone hyperplasia in the distal, mid, and proximal esophagus, respectively. She was referred to the Children's Hospital Eosinophilic Gastrointestinal Disorders clinic for further management. Subsequent skin prick testing showed a positive response to her hydrolyzed milk protein containing formula and her diet was changed to elemental formula. After two months of elemental formula and oral cromolyn sodium, EGD was unchanged with a pale, furrowed esophagus and maximal eosinophil counts of 100, 90, and 70 per hpf in the distal, mid, and proximal esophagus with diffuse basal zone hyperplasia. Her developmental delay precluded the use of a fluticasone inhaler devise with puff and swallow technique. As an alternative, she received oral budesonide 500 micrograms (Pulmicort®) mixed with sucralose (Splenda®) twice daily as topical esophageal therapy. Following 3 months of budesonide, she had improvement in her abdominal pain and EGD revealed a normal appearing esophagus with improved maximum eosinophil counts of 28, 20, and 5 per hpf in the distal, mid, and proximal esophagus and decreased basal zone hyperplasia.

Example 3

Multi-Patient Retrospective Review

This example details the efficacy and safety of once daily oral viscous budesonide (OVB) in inducing and maintaining remission of disease activity in children with EE. The results of this study show that in 20 children (mean age 5.5 yrs) the mean highest eosinophil count was 87 eos/hpf (range 30-170) before and 7 eos/hpf (range 0-50, p<0.0001) after therapy. There were 16 (80%) responders, 1 partial-responder and 3 non-responders. The mean symptom score fell from 4.4 to 0.8 (p<0.0001) and the mean endoscopy score fell from 3.6 to 0.8 (p<0.0001). No significant adverse events were reported. Morning cortisol levels were within normal limits.

Methods.

This retrospective review was approved by Children's Hospital, San Diego (CHSD) and University of California at San Diego (UCSD), Human Research Protection Program. Patients were referred from CHSD subspecialty clinics and other institutions to the EE clinic. Some patients received previous therapy with proton pump inhibitor, elimination diet based upon skin or blood allergy testing, elimination diet or topical fluticasone proprionate only after the diagnosis of EE was established. Patients who received these therapies, refused elimination diet, or were unable to utilize fluticsone prorionate MDI but continued to have ≧24 eos/hpf on esophageal biopsy were offered OVB. Patients were defined as having food or aeroallergen sensitization if RAST and/or skin prick testing were positive. No changes were made to longstanding therapy used for treating chronic conditions such as asthma or eczema and none of the children received concurrent immune-modulatory treatment. Morning cortisol measurements were available only in 13 patients as this test was not initially performed routinely.

Figure 1:
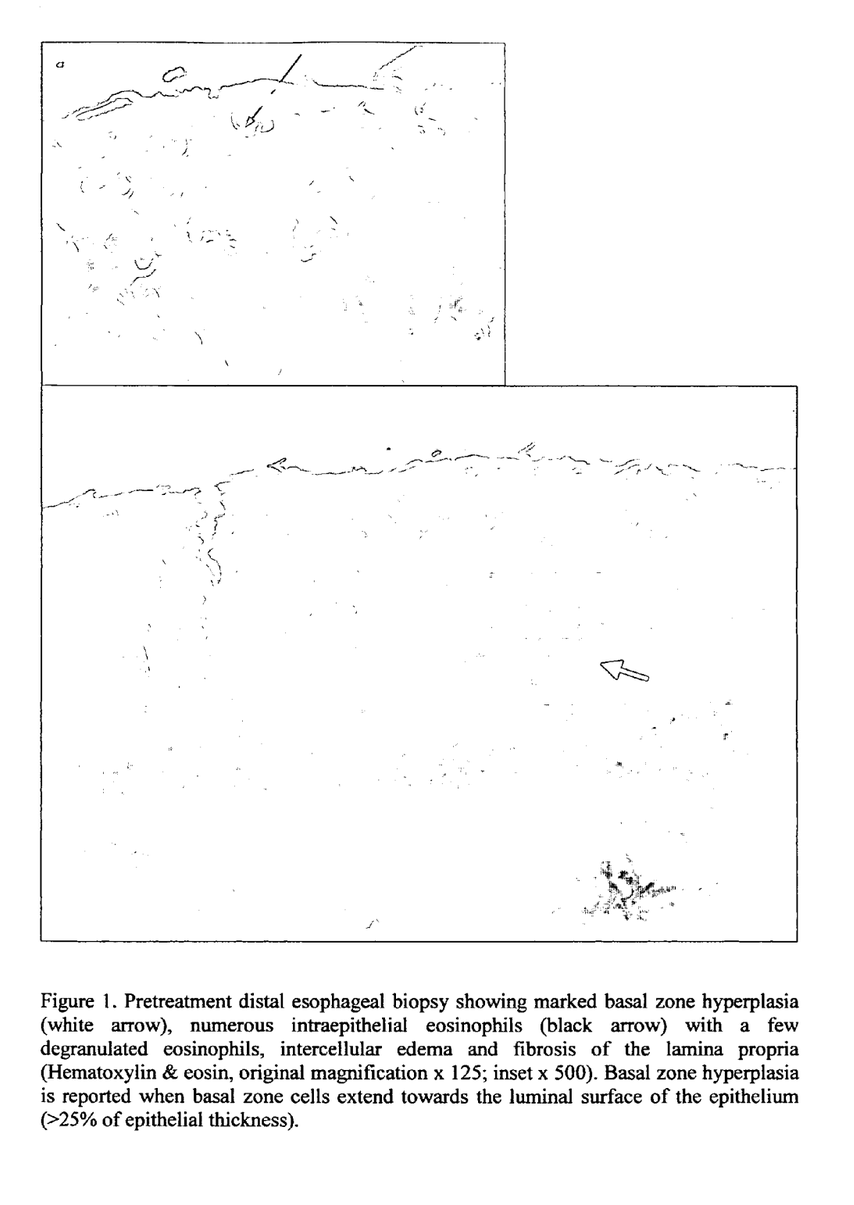
FIG. 1: Pretreatment distal esophageal biopsy showing marked basal zone hyperplasia (white arrow), numerous intraepithelial eosinophils (black arrow) with a few degranulated eosinophils, intercellular edema and fibrosis of the lamina propria (Hematoxylin & eosin, original magnification×125; inset×500). Basal zone hyperplasia is reported when basal zone cells extend towards the luminal surface of the epithelium (>25% of epithelial thickness).
Figure 2:
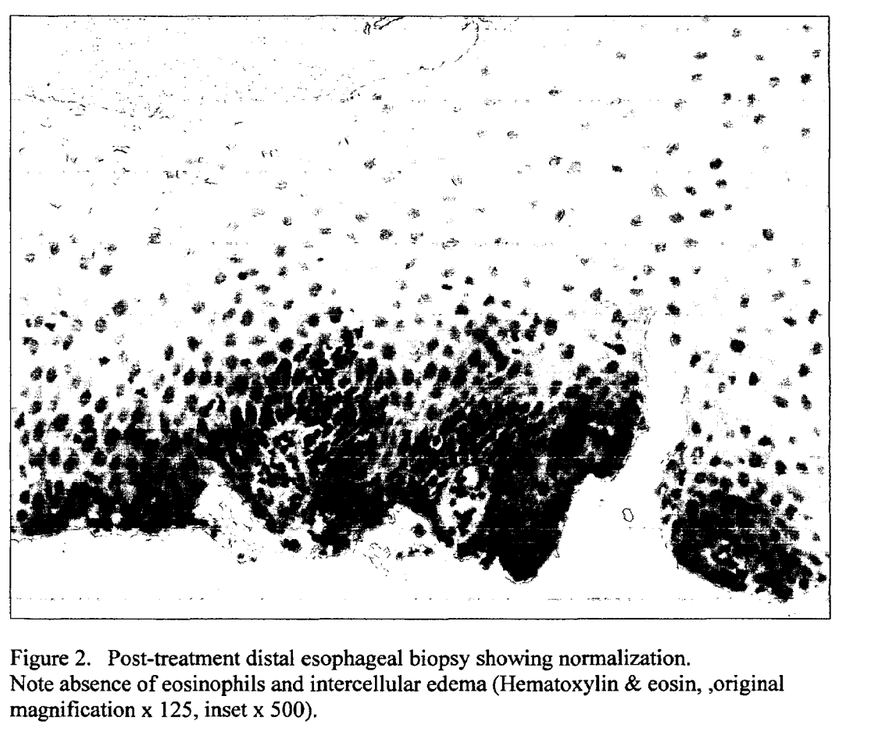
FIG. 2: Post-treatment distal esophageal biopsy showing normalization. Note absence of eosinophils and intercellular edema (Hematoxylin & eosin, original magnification×125, inset×500).
Figure 3:
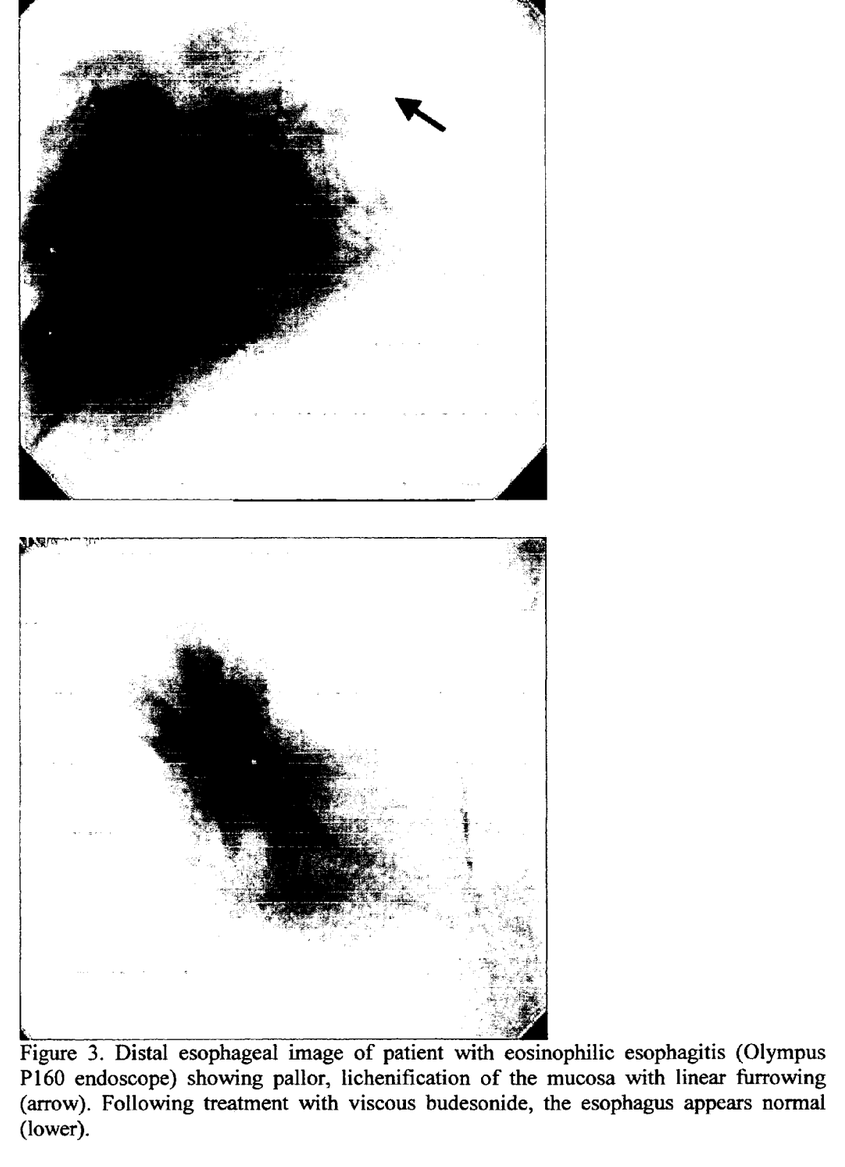
FIG. 3: Distal esophageal image of patient with eosinophilic esophagitis (Olympus P160 endoscope) showing pallor, lichenification of the mucosa with linear furrowing (arrow). Following treatment with viscous budesonide, the esophagus appears normal (lower).

Upper Gastrointestinal Endoscopy and Biopsy. Endoscopy was performed using the Olympus P160 endoscope (by RD) and pan-esophageal, gastric and duodenal biopsies were taken. Eosinophilic esophagitis was diagnosed when ≧24 eos/hpf were found in at least one of the esophageal sites biopsied. Two mucosal biopsies were taken from the proximal esophagus (3 cm below the crycopharyngeus muscle), distal esophagus (3 cm above the gastroesophageal junction (GEJ), and mid-esophagus (midpoint between the crycopharyngeus muscle and the GEJ). Biopsies were processed routinely and evaluated by a pediatric pathologist (RN). The highest number of eosinophils per ×400 high power field were counted [FIG. 1]. Basal zone hyperplasia (BZH) is reported when basal zone cells extend towards the luminal surface of the epithelium (>25% of epithelial thickness).

Follow-up endoscopy with biopsies were taken after 3-4 months treatment OVB. Counting the highest number of eos/hpf within biopsies determined the response to therapy and patients were categorized into responders (0-7 eos/hpf), partial-responders (8-23 eos/hpf) and non-responders (≧24 eos/hpf).

An EE Endoscopy Score was devised to compare findings before and after treatment. It was calculated from procedure reports and photographs. Four categories, (1) pallor and diminished vascular markings; (2) furrowing with "thickened" mucosa; (3) white mucosal plaques; (4) concentric rings or strictures. For each category, one point was allocated if 1 or 2 esophageal sites were involved, and two points for pan-esophageal involvement. The maximum score was 8.

Treatment. Patients received OVB 0.5 to 2 mg daily and were instructed not to ingest any solids or liquids for 30 minutes afterwards. Viscous budesonide was made by mixing each 0.5 mg Pulmicort™ respule with 5 grams (5 packets) of sucralose (Splenda™) to create a volume of 8-12 ml. A Pulmicort Respule™ is liquid budesonide intended for nebulized administration (0.5 mg budesonide/2 ml). No dietary changes were made in patients already on dietary restrictions. All patients received concurrent acid-suppression therapy.

Symptoms. A modified symptom score based on children with acid-peptic disease is used routinely in the EE clinic (31). The symptom categories include (1) heartburn or regurgitation; (2) abdominal pain or unexplained irritability in younger children; (3) nausea or vomiting; (4) anorexia or early satiety; (5) dysphagia or odynophagia, (6) nocturnal wakening with symptoms; (7) gastrointestinal bleeding (previous 4 months). Each category scored 0-2 points with a maximum of 14 points. Zero points were awarded if the symptom was absent; one point if the symptom was mild, did not interfere with daily activities; 2 points if the symptoms were severe enough to interrupt daily activities. Previous GI bleeding was considered mild (1 point) if there was no associated hemodynamic compromise or anemia, and severe (2 points) if bleeds were multiple, caused anemia, or required blood transfusion.

Statistical Analysis.

All statistical analysis was carried out using NCSS Statistical Softward Package. Two-tailed p values were calculated using paired t-tests to compare the means of patient values for eos/hpf, EE Endoscopy Scores and Symptom Scores before and after budesonide therapy. Two-tailed unpaired t-tests were utilized in order to compare variables grouped by responders versus non-responders. Spearman's correlation coefficients were generated using GraphPad Prism software. Results with p values<0.05 were considered statistically significant. Both mean and median statistics were generated, both were equivalent and mean statistics are presented.

Results.

Subjects. Chart reviews were undertaken on twenty children with a mean age of 5.5 years (range 1.7 to 17.6 yrs). Fifteen were Caucasian, 2 Hispanic, 2 Asian, and 1 African American. Three children had developmental delay (1 cerebral palsy, 1 autism, 1 Rett's Syndrome) and one had mild IgG deficiency (321 mg/dl, reference range 423-1090 mg/dl). None had *H. pylori* infection. Fourteen children had asthma, eczema and/or allergic rhinitis, 16 had sensitization to foods based on positive skin and/or RAST testing (Table 1). Prior to OVB, 6 children received a restriction diet (3 with concurrent elemental formula), 5 received topical fluticasone proprionate and 5 children received proton pump inhibitor (PPI) therapy. An additional 5 children received PPI therapy with either fluticasone proprionate or diet. All of these previously treated children had >24 eos/hpf on repeat esophageal biopsy before starting OVB therapy. [Table 1].

Mean morning cortisol levels measured in 18 patients was 9.5 ug/dL (patient range 6-17 ug/dL, normal range 2-17 ug/dL,). Seventeen children gained weight during treatment at a mean rate of 0.42 kg/month. No adverse effects attributable to OVB were noted except for one child with low IgG who developed esophageal candida.

Treatment. Patients received OVB for a mean of 3.6 months before repeat endoscopy. Fifteen patients received OVB 1 mg/day, four received 2 mg/day and one unintentionally received 0.5 mg/day [Table 1]. In some embodiments of the invention, 0-1 mg/day, 1-2 mg/day, 2-3 mg/day, 34 mg/day, 4-5 mg/day, or 5-6 mg/day of corticosteroid, for example topical corticosteroid, for example, Budesonide, are administered to a patient.

Histology. Before treatment the mean highest eosinophil count for all patients, for all sites was 87 eos/hpf (95% CI 72-103), with a mean of 80 eos/hpf (95% CI 66-94) in the distal, 53 eos/hpf (95% CI 37-68) in the mid and 43 eos/hpf (95% CI 24-61) in the proximal esophagus. The highest eosinophil count was found in distal esophageal biopsies in 14, mid-esophageal in 3 and proximal esophageal biopsies in 3 patients. Ten patients (50%) had pan-esophageal BZH. The mean highest gastric and duodenal eosinophil count was 1 eos/hpf (range 0-5). Following treatment, the mean highest eosinophil count for all patients was 7 eos/hpf (95% CI 1-13, p<0.0001). All patients had a decreased eosinophil count with mean levels of 9 (95% CI 9-14) in distal, 5 (95% CI 1-9) in mid and 2 eos/hpf (95% CI 1-5) in the proximal esophagus. Sixteen patients were histologic responders, 1 partial-responder and 3 were non-responders (Table 1 and 2). There was no difference in age, height, dose, or duration of therapy between the 16 histologic responders and the 4 partial or non-responders. One partial-responder had received OVB 0.5 mg/day; his highest count fell from 100 to 16 eos/hpf. The three non-responders still demonstrated 50-80% improvement in their highest counts with treatment (Tables 1 and 2). Of the 5 patients who were non-responders to fluticasone proprionate, 3 were histologic responders, 1 was a partial-responder and 1 was a non-responder to OVB therapy; the non-responder still had a >70% drop in highest eosinophil count during treatment [Table 1].

Basal zone hyperplasia resolved completely in 6 of the 10 children with pan-esophageal findings. These patients were all histologic responders (Table 1).

Upper Gastrointestinal Endoscopy. Before treatment, the mean EE Endoscopy Score for all patients was 3.6 (range 1-6). The commonest findings were pallor (90%), linear furrowing (80%) and white plaques (50%). Following treatment the mean EE Endoscopy Score was 0.8 (range 0-5). The EE Endoscopy Score fell to 0 in twelve children and improved in nineteen. Eleven with complete normalization were histologic responders and 1 was a non-responder (>70% fall in eosinophil count). One child with an EE Endoscopy Scores that did not improve was a histologic non-responder. (Tables 1, 2, 3).

Symptom Score. Before treatment the mean symptom score for all patients was 4.4 and following treatment fell to 0.8 (p<0.0001). Eighteen children had an improved symptom score and 11 had a score of 0. Eight of these 11 patients were histologic responders with complete endoscopic resolution. Two children had symptom scores of 0 before and after OVB therapy. Although these 2 children had symptom resolution on elimination diet or fluticasone, histologic resolution did not occur until after treatment with OVB. The 5 patients who took only PPI therapy prior to budesonide did not have a significant improvement of symptoms on acid-suppression therapy alone (Tables 1, 2, 4).

There was a statistically significant correlation between the number of eosinophils and the Endoscopy and Symptom scores (Spearman r of 0.64 and 0.84 for the maximum eosinophil count and Symptom and Endoscopy score, respectively [p<0.0001]).

Discussion.

Eosinophilic esophagitis is a disorder of the esophagus which is becoming increasingly recognized (8, 14, 16, 17, 32-35). The annual incidence of the condition has been estimated at 1 in 10,000 children (35), but even this number may be an underestimate. The pathogenesis of EE is still poorly understood; allergic and abnormal host immunologic responses have been suggested. Therapeutic treatment options for EE have included dietary restriction/elemental diet, systemic and topical corticosteroids (2, 22-30). There is, however, presently no topical steroid designed for esophageal drug therapy. Twice daily ingested fluticasone propionate administered through an MDI is currently the most widely accepted topical therapy for EE. This therapy, however, may be particularly problematic for younger children and those with developmental delay who are unlikely to utilize the puff and swallow technique effectively (36). In this example, 10 of 13 children who were under the age of 5 and/or had developmental delay were responders to OVB therapy. The 3 non-responders still demonstrated a 50-80% reduction in esophageal eosinophil count; all had symptomatic improvement and 2 had endoscopic improvement. In addition to this, of the 5 children (ages 3-9 yrs) who previously failed to respond to swallowed fluticasone proprionate therapy, 3 had pan-esophageal histologic normalization with OVB and the other 2 had >75% reduction in esophageal eosinophil count.

These data suggest that following OVB therapy there is a strong correlation between the fall in esophageal eosinophil levels and the improvement in the Endoscopy and Symptom Score. This suggests that these scoring tools are useful clinical measures in pediatric EE but further prospective studies will need to be done in order to validate these tools. Eighteen (90%) of the patients, including the partial-responder and one non-responder, had improved Endoscopy Scores and all symptomatic children had improved Symptom Scores. This may be because the partial-responder and even the three non-responders had a 50-80% reduction in their highest esophageal eosinophil count following OVB treatment. The correlation between the severity of symptoms and of esophageal eosinophilic infiltration is not always so clear-cut. Two initially symptomatic children (#7 and 13, table 1) were asymptomatic before budesonide therapy despite having continued esophageal eosinophilic infiltration (80-120 eos/hpf). One child was a histologic non-responder to elimination diet and the other to topical fluticasone proprionate with PPI therapy, both for 3 months. These two children remained asymptomatic during budesonide therapy. This disassociation between symptoms and histologic disease is not unique to these two study patients. In our practice we have treated adolescents who, having initially responded symptomatically and histologically to ingested fluticasone proprionate, became non-compliant to therapy, claimed to be asymptomatic, but on routine follow-up evaluation had endoscopic and histologic recurrence of disease. The exact reason for this remains unclear. Children may become accustomed to their symptoms and not complain. Alternatively, they may conceal their symptoms because of an unwillingness to continue therapy or fear of undergoing further tests such as endoscopy. Another possibility is that eosinophilic infiltration may not always cause symptoms, even within the same individual. This could explain why some patients only complain of symptoms after esophageal stricturing has occurred.

Most patients with EE are thought to have allergy-mediated disease, triggered by food and/or aeroallergens (2-4). However, 20% of the study patients had no evidence of IgE-mediated sensitization to foods or aeroallergens, and this concurs with other reported estimates of EE occurring in non-atopic individuals (17, 21, 35). Skin and patch testing can suggest causative food allergens in over half of the patients with EE, but not all will respond symptomatically or histologically to dietary restrictions (22). Amino-acid based formulas have been shown to be effective (2, 24, 37), but many children find the formula non-palatable and often require feeding through a naso-gastric or gastrostomy tube. In addition, after re-introducing new foods to children on elemental diets, patients require regular repeat UGI endoscopy to confirm continued control of inflammation. This example shows that children with EE, both with and without identifiable food/aero allergies respond well to OVB therapy and most are able to tolerate entirely normal diets. The dosing of OVB was based upon the therapeutic recommendations for asthmatic children. Most of the patients responded to 1 mg daily, but two patients needed 2 mg a day before a response was seen. All patients tested, including those taking OVB 2 mg daily, had normal morning cortisol levels and were therefore unlikely to have significant adrenal suppression. This may be because budesonide absorbed intestinally undergoes rapid hepatic metabolism.

Although there is conflicting data from pediatric and adult studies, with reports of negative 24 hr pH studies in children with EE, many patients will have at least a partial symptomatic response to acid-suppression therapy (1, 7, 17, 30, 38). Acid-suppression therapy alone will not, however, significantly alter the histologic findings and persisting esophageal eosinophilia may ultimately lead to esophageal narrowing in 10-30% of cases (14, 18, 20, 21). This lack of histologic response to PPI therapy in patients with EE was confirmed in 10 of the study patients. Before starting all patients on OVB therapy, eosinophils were more abundant and basal zone hyperplasia more prominent in distal, as compared with mid and proximal esophageal biopsies (80, 53 and 43 eos/hpf, respectively for tissue eosinophils and 95%, 75% and 65% of biopsies for BZH, respectively). The reason for this distal-predominance is unclear, but most likely supports the argument that GER does co-exist with EE, particularly as BZH and mild tissue eosinophilia also occur in reflux esophagitis. Therefore, all patients treated with OVB also received acid-suppression therapy.

These data suggest that oral viscous budesonide would be an effective and safe treatment for individuals, for example children, for example, young children, with proven EE. It may have advantages over other therapies in that it is palatable, its volume (8-12 ml) provides pan-esophageal mucosal coverage and it requires only once daily administration A larger placebo-controlled clinical trials would provide more information about dosing, efficacy and long-term safety of this treatment.

TABLE 1

Patient characteristics pre- and post-viscous Budesonide (Budes.) therapy.
Patient response was determined by counting the highest eosinophil count/hpf after viscous budesonide and categorized into responders (0–7 eos/hpf), partial-responders (8–23 eos/hpf) and non-responders (≧24 eos/hpf).

| Pt. | Age mths | Res*** | Sex | ΔWt**** | IgE* | Prior** mths | PPI before Budes. | Budes Dose mths | Highest Eos. count/hpf Pre/Post Budesonide | | | Basal Zone Hyperplasia (site+) | | Endoscopy Score | | Symptom Score | |
|---|---|---|---|---|---|---|---|---|---|---|---|---|---|---|---|---|---|
| | | | | | | | | | Site+ | Pre | Post | Pre | Post | Pre | Post | Pre | Post |
| 1 | 42 | R | M | −0.1 | F, A | ELIM (4) | No | 1 mg (4) | M | 70 | 1 | Yes (P, M, D) | Yes (P, M) | 6 | 1 | 3 | 2 |
| 2 | 33 | R | M | 0.15 | X | | No | 1 mg (3) | D | 30 | 7 | Yes (D) | Yes (D) | 1 | 0 | 7 | 3 |
| 3 | 71 | R | M | 0.73 | F, A | | Yes | 1 mg (3) | D | 74 | 0 | Yes (P, D) | No | 2 | 0 | 5 | 0 |
| 4 | 109 | R | M | 0.85 | X | FLU (3) | Yes | 1 mg (4) | M | 100 | 2 | Yes (M, D) | No | 4 | 2 | 4 | 0 |
| 5 | 41 | R | M | −0.07 | F, A | ELIM (2) | Yes | 1 mg (3) | D | 50 | 0 | Yes (M, D) | No | 2 | 1 | 8 | 3 |

TABLE 1-continued

Patient characteristics pre- and post-viscous Budesonide (Budes.) therapy.
Patient response was determined by counting the highest eosinophil count/hpf after viscous budesonide and categorized into responders (0–7 eos/hpf), partial-responders (8–23 eos/hpf) and non-responders (≧24 eos/hpf).

| Pt. | Age mths | Res*** | Sex | ΔWt**** | IgE* | Prior** mths | PPI before Budes. | Budes Dose mths | Site+ | Highest Eos. count/hpf Pre | Post | Basal Zone Hyperplasia (site+) Pre | Post | Endoscopy Score Pre | Post | Symptom Score Pre | Post |
|---|---|---|---|---|---|---|---|---|---|---|---|---|---|---|---|---|---|
| 6 | 66 |   | M |   | F, A | FLU (3) |   | 1 mg (3) | P | 60 | 50 |   |   | 6 | 1 | 4 | 3 |
|   |   | R | M | 0.5 | F, A |   | Yes | 2 mg (3) | P | 50 | 0 | Yes (M) | No | 1 | 0 | 3 | 2 |
| 7 | 88 |   | M |   | F, A | FLU (12) | Yes | 1 mg (3) | D | 50 | 80 |   |   | 4 | 4 | 0 | 0 |
|   |   | R |   | 0.375 |   |   | Yes | 2 mg (3) | D | 80 | 1 | Yes (P, M, D) | No | 4 | 0 | 0 | 0 |
| 8 | 90 | R | F | 0.65 | X |   | No | 1 mg (4) | P | 170 | 0 | Yes (P, D) | No | 6 | 1 | 9 | 0 |
| 9 | 41 | R | M | 0.18 | A |   | Yes | 1 mg (4) | P, D | 70 | 0, 0 | Yes (P, M, D) | No | 2 | 0 | 3 | 0 |
| 10 | 20 | R | M | 0.03 | F |   | Yes | 1 mg (4) | D | 80 | 0 | Yes (P, M, D) | No | 4 | 0 | 3 | 0 |
| 11 | 201 | R | F | 0.1 | A |   | No | 2 mg (4) | D | 130 | 0 | Yes (P, M, D) | No | 6 | 0 | 5 | 1 |
| 12 | 34 | R | M | −0.15 | X |   | No | 1 mg (3) | D | 100 | 0 | Yes (P, M, D) | No | 5 | 0 | 3 | 0 |
| 13 | 51 | R | F | 0.08 | F | ELIM (5) | No | 1 mg (6) | D | 120 | 0 | Yes (D) | No | 2 | 0 | 0 | 0 |
| 14 | 48 | R | M | 1.5 | F | ELIM (5) | No | 1 mg (3) | D, M, P | 30 | 0 | Yes (P, M, D) | No | 4 | 0 | 3 | 0 |
| 15 | 31 | R | M | 0.2 | F | ELIM (3) | Yes | 1 mg (4) | D | 100 | 5 | Yes (P, D) | No | 2 | 0 | 7 | 0 |
| 16 | 121 | R | M | 0.13 | F, A |   | Yes | 2 mg (3) | M | 90 | 3 | Yes (P, M, D) | Yes (P, M, D) | 4 | 2 | 4 | 1 |
| 17 | 36 | P | M | 0.46 | F, A | FLU (12) | No | 0.5 mg (3) | D | 100 | 16 | Yes (M, D) | No | 6 | 1 | 6 | 2 |
| 18 | 32 | N | M | 0.83 | F |   | No | 1 mg (3) | D | 100 | 50 | Yes (M, D) | Yes (P, D) | 2 | 3 | 3 | 1 |
| 19 | 68 | N | F | 0.15 | F | ELIM (2) | Yes | 1 mg (4) | D | 100 | 28 | Yes (P, M, D) | Yes (P, M, D) | 4 | 0 | 2 | 0 |
| 20 | 93 | N | M | 0.15 | F, A | FLU |   No | 1 mg (4) | D | 100 | 25 | Yes (P, M, D) | Yes (P, M, D) | 5 | 2 | 8 | 0 |

Patient 6 and 7 failed treatment with 1 mg viscous budesonide, but responded to an increased dose. Patient 11 was started on 2 mg viscous budesonide because of her age and size. Patient 16 had dose increased from 1 mg to 2 mg viscous budesonide after one month because symptoms persisted on lower dose.
*Specific IgE. Sensitization to food (F) or aeroallergens (A) as determined by RAST or skin-prick testing. X = none.
**Prior therapy was with elimination diet (ELIM), topical fluticasone proprionate and/or proton pump inhibitors (PPI).
+Site of esophageal involvement is divided into distal (D), mid (M), and proximal (P).
***Response Category R = Responder, N = Non-Responder, P = Partial Responder.
****Weight change per month. mths = months.
The highest eosinophil count/hpf, presence of basal zone hyperplasia, endoscopy and symptom scores are given pre- and post-viscous budesonide therapy.
Maximum Endoscopy Score is 8 and maximum Symptom Score is 14.

TABLE 2

Esophageal eosinophil count pre- and post-viscous budesonide for different patient response categories.. Mean values and standard error of the mean (SEM) in parenthesis are provided for the highest esophageal eosinophil counts (eos/hpf) measured within the whole esophagus and different sites.

| Response Category | Esophagus Eos/hpf Mean (SEM) Pre | Post | Proximal Esophagus Eos/hpf Pre | Post | Mid Esophagus Eos/hpf Pre | Post | Distal Esophagus Eos/hpf Pre | Post |
|---|---|---|---|---|---|---|---|---|
| Responders N = 16 | 84 (9) | 1.4** (0.6) | 41 (11) | 1* (0.5) | 49 (8) | 1** (0.5) | 75** (8) | 3 (1) |
| Partial-responder N = 1 | 100 | 20 | 50 | 20 | 60 | ND | 100 | 16 |

TABLE 2-continued

Esophageal eosinophil count pre- and post-viscous budesonide for different patient response categories.. Mean values and standard error of the mean (SEM) in parenthesis are provided for the highest esophageal eosinophil counts (eos/hpf) measured within the whole esophagus and different sites.

| Response Category | Esophagus Eos/hpf Mean (SEM) | | Proximal Esophagus Eos/hpf | | Mid Esophagus Eos/hpf | | Distal Esophagus Eos/hpf | |
|---|---|---|---|---|---|---|---|---|
| | Pre | Post | Pre | Post | Pre | Post | Pre | Post |
| Non-responders N = 3 | 100 (0) | 34* (8) | 50 (25) | 6 (2) | 68 (17) | 19 (4) | 100 (0) | 34* (8) |

*$p < 0.05$
**$p < 0.001$, Categories without asterisks do not reach statistical significance.

TABLE 3

Eosinophilic esophagitis Endoscopy Scores, pre- and post-viscous budesonide therapy, for different response categories.

| Response Category | Total Score Mean (SEM) | | Pallor Mean (SEM) | | Furrows Mean (SEM) | | Plaques Mean (SEM) | | Esophageal Rings | |
|---|---|---|---|---|---|---|---|---|---|---|
| | Pre | Post | Pre | Post | Pre | Post | Pre | Post | Pre | Post |
| Responders N = 16 | 3.4 (0.4) | 0.4** (0.2) | 1.4 (0.2) | 0.3** (0.2) | 1.3 (0.2) | 0.2** (0.1) | 0.8 (0.2) | 0* (0) | None | None |
| Partial-responder N = 1 | 6 | 1 | 2 | 0 | 2 | 1 | 2 | 0 | None | None |
| Non-responders N = 3 | 3.7 (0.9) | 1.7 (0.9) | 1.7 (0.3) | 0.7* (0.3) | 1 (0.6) | 0.3 (0.3) | 1 (0.6) | 0.3 (0.3) | None | None |

Maximum total score is 8 and maximum for each category is 2.
Standard error of mean shown in parathesisis.
*$p < 0.05$
**$p < 0.001$,
Categories without asterisks do not reach statistical significance.

TABLE 4

Symptom Score, pre- and post-viscous budesonide therapy for different response categories.

| Cat. | Total Score Mean (SEM) | | Heartburn | | Pain | | Nausea/Vomiting | | Dysphagia | | Nocturnal Wakening | | Anorexia | | GI Bleed | |
|---|---|---|---|---|---|---|---|---|---|---|---|---|---|---|---|---|
| | Pre | Post | Pre | Post | Pre | Post | Pre | Post | Pre | Post | Pre | Post | Pre | Post | Pre | Post |
| R N = 16 | 4.2 (0.6) | 0.75** (0.3) | 1 (0.2) | 0.1** (0.1) | 0.8 (0.2) | 0.2* (0.1) | 1.4 (0.2) | 0.1** (0.1) | 0.2 (0.1) | 0.1 (1) | 0.2 (0.2) | 0 (0) | 0.6 (0.2) | 0.3 (0.2) | None | None |
| P N = 1 | 6 | 2 | 2 | 1 | 2 | 1 | 2 | 0 | 0 | 0 | 0 | 0 | 0 | 0 | None | None |
| N N = 3 | 5.5* (2.5) | 0.5* (0.5) | 1.5 (0.5) | 0.5 (0.5) | 1.5 (0.5) | 0 (0) | 1.5 (0.5) | 0 (0) | 1 (1) | 0 (0) | 0 | 0 | 0 | 0 | None | None |

Maximum total score is 14 and maximum for each category is 2.
Standard error of mean shown in parathesisis.
*$p < 0.05$
**$p < 0.001$,
Categories without asterisks do not reach statistical significance.
Cat.: Response Category:
R = Responders,
P = Partial-Responder,
N = Non-Responders 1. Liacouras C A, Ruchelli E. Eosinophilic esophagitis. Cuff Opin Pediatr 2004; 16:560-6.
2. Kelly K J, Lazenby A J, Rowe P C, et al. Eosinophilic esophagitis attributed to gastroesophageal reflux: improvement with an amino acid-based formula. Gastroenterology 1995; 109: 1503-12.
3. Fogg M I, Ruchelli E, Spergel J M. Pollen and eosinophilic esophagitis. J Allergy Clin Immunol 2003; 112:796-7.
4. Mishra A, Hogan S P, Brandt E B, Rothenberg M E. An etiological role for aeroallergens and eosinophils in experimental esophagitis. J Clin Invest 2001; 107:83-90.
5. Spergel J M, Beausoleil J L, Mascarenhas M, Liacouras C A. The use of skin prick tests and patch tests to identify causative foods in eosinophilic esophagitis. J Allergy Clin Immunol 2002; 109:363-8.

6. Ruchelli E, Wenner W, Voytek T, et al. Severity of esophageal eosinophilia predicts response to conventional gastroesophageal reflux therapy. Pediatr Dev Pathol 1999; 2:15-8.
7. Steiner S J, Gupta S K, Croffie J M, Fitzgerald J F. Correlation between number of eosinophils and reflux index on same day esophageal biopsy and 24 hour esophageal pH monitoring. Am J Gastroenterol 2004; 99:801-5.
8. Orenstein S R, Shalaby T M, Di Lorenzo C, et al. The spectrum of pediatric eosinophilic esophagitis beyond infancy: a clinical series of 30 children. Am J Gastroenterol 2000; 95:1422-30.
9. Rothenberg M E, Mishra A, Collins M H, Putnam P E. Pathogenesis and clinical features of eosinophilic esophagitis. J Allergy Clin Immunol 2001; 108:891-4.
10. Ravelli A M, Villanacci V, Ruzzenenti N, et al. Dilated Intercellular Spaces: A Major Morphological Feature of Esophagitis. J Pediatr Gastroenterol Nutr 2006; 42:510-515.
11. Steiner S J, Kernek K M, Fitzgerald J F. Severity of Basal Cell Hyperplasia Differs in Reflux Versus Eosinophilic Esophagitis. J Pediatr Gastroenterol Nutr 2006; 42:506-509.
12. Mueller S, Aigner T, Neureiter D, Stolte M. Eosinophil infiltration and degranulation in esophageal mucosa from adult patients with eosinophilic esophagitis (EE). A retrospective comparative pathologic biopsy study. J Clin Pathol 2006. E-pub before publication.
13. Croese J, Fairley S K, Masson J W, et al. Clinical and endoscopic features of eosinophilic esophagitis in adults. Gastrointest Endosc 2003; 58:516-22.
14. Aceves S N R, Dohil R, Schwimmer J, Bastian J. Distinguishing Eosinophilic Esophagitis in pediatric patients: clinical, endoscopic, and histologic features of an emerging disorder. Journal of Clinical Gastroenterology. 2006. *In press*
15. Straumann A, Simon H U. Eosinophilic esophagitis: escalating epidemiology? J Allergy Clin Immunol 2005; 115: 418-9.
16. Cherian S, Smith N M, Forbes D A. Rapidly increasing prevalence of eosinophilic oesophagitis in Western Australia. Arch Dis Child 2006 E-pub before publication.
17. Sant'Anna A M, Rolland S, Fournet J C, et al. Eosinophilic Esophagitis in Children: Symptoms, Histology and pH Probe Results. J Pediatr Gastroenterol Nutr 2004; 39:373-377.
18. Potter J W, Saeian K, Staff D, et al. Eosinophilic esophagitis in adults: an emerging problem with unique esophageal features. Gastrointest Endosc 2004; 59:355-61.
19. Parfitt J R, Gregor J C, Suskin N G, et al. Eosinophilic esophagitis in adults: distinguishing features from gastroesophageal reflux disease: a study of 41 patients. Mod Pathol 2006; 19:90-6.
20. Desai T K, Stecevic V, Chang C H, et al. Association of eosinophilic inflammation with esophageal food impaction in adults. Gastrointest Endosc 2005; 61:795-801.
21. Straumann A, Spichtin H P, Grize L, et al. Natural history of primary eosinophilic esophagitis: a follow-up of 30 adult patients for up to 11.5 years. Gastroenterology 2003; 125:1660-9.
22. Spergel J M, Andrews T, Brown-Whitehorn T F, et al. Treatment of eosinophilic esophagitis with specific food elimination diet directed by a combination of skin prick and patch tests. Ann Allergy Asthma Immunol 2005; 95:336-43.
23. Kagalwalla A F, Sentongo T A, Ritz S, et al. Effect of six-food elimination diet on clinical and histologic outcomes in eosinophilic esophagitis. Clin Gastroenterol Hepatol 2006; 4:1097-102.
24. Markowitz J E, Spergel J M, Ruchelli E, Liacouras C A. Elemental diet is an effective treatment for eosinophilic esophagitis in children and adolescents. Am J Gastroenterol 2003; 98:777-82.
25. Liacouras C A, Wenner W J, Brown K, Ruchelli E. Primary eosinophilic esophagitis in children: successful treatment with oral corticosteroids. J Pediatr Gastroenterol Nutr 1998; 26:380-5.
26. Teitelbaum J E, Fox V L, Twarog F J, et al. Eosinophilic esophagitis in children: immunopathological analysis and response to fluticasone propionate. Gastroenterology 2002; 122:1216-25.
27. Faubion W A, Jr., Perrault J, Burgart L J, et al. Treatment of eosinophilic esophagitis with inhaled corticosteroids. J Pediatr Gastroenterol Nutr 1998; 27:90-3.
28. Aceves S S, Dohil R, Newbury R O, Bastian J F. Topical viscous budesonide suspension for treatment of eosinophilic esophagitis. J Allergy Clin Immunol 2005; 116:705-6.
29. Noel R J, Putnam P E, Collins M H, et al. Clinical and immunopathologic effects of swallowed fluticasone for eosinophilic esophagitis. Clin Gastroenterol Hepatol 2004; 2:568-75.
30. Remedios M, Campbell C, Jones D M, Kerlin P. Eosinophilic esophagitis in adults: clinical, endoscopic, histologic findings, and response to treatment with fluticasone propionate. Gastrointest Endosc 2006; 63:3-12.
31. Dohil R, Newbury R O, Sellers Z M, et al. The evaluation and treatment of gastrointestinal disease in children with cystinosis receiving cysteamine. J Pediatr 2003; 14:224-30.
32. Cheung K M, Oliver M R, Cameron D J, et al. Esophageal eosinophilia in children with dysphagia. J Pediatr Gastroenterol Nutr 2003; 37:498-503.
33. Fox V L, Nurko S, Furuta G T. Eosinophilic esophagitis: it's not just kid's stuff. Gastrointest Endosc 2002; 56:260-70.
34. Budin C, Villard-Truc F, Rivet C, et al. [Eosinophilic esophagitis: 3 case reports]. Gastroenterol Clin Biol 2005; 29:73-5.
35. Noel R J, Putnam P E, Rothenberg M E. Eosinophilic esophagitis. N Engl J Med 2004; 351:940-1.
36. Guajardo J R, Plotnick L M, Fende J M, et al. Eosinophil-associated gastrointestinal disorders: a world-wide-web based registry. J Pediatr 2002; 141:576-81.
37. Liacouras C A, Spergel J M, Ruchelli E, et al. Eosinophilic esophagitis: a 10-year experience in 381 children. Clin Gastroenterol Hepatol 2005; 3:1198-206.
38. Liacouras C A. Eosinophilic esophagitis: treatment in 2005. Curr Opin Gastroenterol 2006; 22:147-152.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Singular forms "a", "an", and "the" include plural reference unless the context clearly dictates otherwise. Thus, for example, reference to "a subset" includes a plurality of such subsets, reference to "a nucleic acid" includes one or more nucleic acids and equivalents thereof known to those skilled in the art, and so forth. The term "or" is not meant to be exclusive to one or the terms it designates. For example, as it is used in a phrase of the structure "A or B" may denote A alone, B alone, or both A and B.

Unless defined otherwise, all technical and scientific terms used herein have the same meanings as commonly understood by one of ordinary skill in the art to which this invention belongs. Although any methods and systems similar or equivalent to those described herein can be used in the practice or testing of the present invention, the methods, devices, and materials are now described. All publications mentioned herein are incorporated herein by reference for the purpose of describing and disclosing the processes, systems, and methodologies which are reported in the publications which might be used in connection with the invention. Nothing herein is to be construed as an admission that the invention is not entitled to antedate such disclosure by virtue of prior invention.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

What is claimed is:

1. A method of reducing or alleviating esophageal inflammation or symptoms associated therewith in an individual in need thereof comprising orally administering a liquid composition as a topical esophageal therapy to said individual, the liquid composition comprising a corticosteroid and at least one excipient that increases the viscosity of the composition, and the liquid composition having a nectar-like to honey-like viscosity.

2. The method of claim 1, wherein the viscosity of the composition is nectar-like.

3. The method of claim 1, wherein said corticosteroid is a topical corticosteroid.

4. The method of claim 1, wherein said corticosteroid is budesonide.

5. The method of claim 1, wherein said individual has eosinophilic esophagitis.

6. The method of claim 1, wherein said individual has been diagnosed with eosinophilic esophagitis.

7. The method of claim 1, wherein said individual is a child.

8. The method of claim 1, wherein said individual is a child less than 16 years old.

9. The method of claim 1, wherein said individual is a child less than 12 years old.

10. The method of claim 1, wherein said individual is a child less than 8 years old.

11. The method of claim 1, wherein said individual is a child less than 6 years old.

12. The method of claim 1, wherein said individual is a child less than 4 years old.

13. The method of claim 1, wherein said individual is a child less than 2 years old.

14. The method of claim 1, wherein 1-6 mg corticosteroid per day is administered to said individual.

15. The method of claim 14, wherein 2-3 mg corticosteroid per day is administered to said individual.

16. The method of claim 14, wherein 1-2 mg corticosteroid per day is administered to said individual.

17. The method of claim 1, wherein about 10-400 μg corticosteroid/kg of said individual per day is administered to said individual.

18. The method of claim 1, wherein the composition is a liquid suspension.

19. The method of claim 1, wherein the individual is a human of any age.

20. The method of claim 1, wherein 0.5-2 mg corticosteroid per day is administered to said individual.

21. The method of claim 1, wherein a therapeutically effective amount of 6 mg/day or less of corticosteroid is administered.

22. The method of claim 1, wherein said excipient comprises lactose, sucrose, cellulose preparations, mannitol, sorbitol, honey, maize starch, wheat starch, rice starch, potato starch, gelatin, gum tragacanth, methyl cellulose, hydroxypropylmethyl-cellulose, sodium carboxymethyl-cellulose (CMC), polyvinylpyrrolidone (PVP: povidone), or a combination thereof.

23. A method of reducing or eliminating esophageal eosinophils in an individual in need thereof comprising topically delivering to the esophagus of said individual a liquid composition comprising a corticosteroid and at least one excipient that increases the viscosity of the composition, and the liquid composition having a nectar-like to honey-like viscosity.

24. The method of claim 23, wherein the viscosity of the composition is nectar-like.

25. The method of claim 23, wherein said corticosteroid is a topical corticosteroid.

26. The method of claim 23, wherein said corticosteroid is budesonide.

27. The method of claim 23, wherein said individual has eosinophilic esophagitis.

28. The method of claim 23, wherein 1-6 mg corticosteroid per day is administered to said individual.

29. The method of claim 28, wherein 2-3 mg corticosteroid per day is administered to said individual.

30. The method of claim 28, wherein 1-2 mg corticosteroid per day is administered to said individual.

31. The method of claim 23, wherein a therapeutically effective amount of 6 mg/day or less of corticosteroid is administered.

32. The method of claim 23, wherein 0.5-2 mg corticosteroid per day is administered to said individual.

33. The method of claim 23, wherein about 10-400 μg corticosteroid/kg of said individual per day is administered to said individual.

34. The method of claim 23, wherein the composition is a liquid suspension.

35. A method of improving or resolving symptoms associated with eosinophilic infiltration of the esophagus in an individual in need thereof comprising topically delivering to the esophagus of said individual a liquid composition comprising a corticosteroid and at least one excipient that increases the viscosity of the composition, and the liquid composition having a nectar-like to honey-like viscosity.

36. The method of claim 35, wherein the viscosity of the composition is nectar-like.

37. The method of claim 35, wherein said corticosteroid is a topical corticosteroid.

38. The method of claim 35, wherein said corticosteroid is budesonide.

39. The method of claim 35, wherein said individual has eosinophilic esophagitis.

40. The method of claim 35, wherein 1-6 mg corticosteroid per day is administered to said individual.

41. The method of claim 40, wherein 2-3 mg corticosteroid per day is administered to said individual.

42. The method of claim 40, wherein 1-2 mg corticosteroid per day is administered to said individual.

43. The method of claim 35, wherein a therapeutically effective amount of 6 mg/day or less of corticosteroid is administered.

44. The method of claim 35, wherein 0.5-2 mg corticosteroid per day is administered to said individual.

45. The method of claim 35, wherein about 10-400 μg corticosteroid/kg of said individual per day is administered to said individual.

46. The method of claim 35, wherein the composition is a liquid suspension.

47. The method of claim 1, wherein the liquid composition comprises a corticosteroid in the absence of another pharmaceutically active ingredient.

48. The method of claim 23, wherein the liquid composition comprises a corticosteroid in the absence of another pharmaceutically active ingredient.

49. The method of claim 35, wherein the liquid composition comprises a corticosteroid in the absence of another pharmaceutically active ingredient.

50. The method of one of claim 1, 23 or 35, wherein said liquid composition comprises a liquid vehicle, wherein said liquid vehicle comprises water.

* * * * *